United States Patent [19]

Mori et al.

[11] Patent Number: 5,596,266
[45] Date of Patent: Jan. 21, 1997

[54] METAL PARTICLE DETECTING SENSOR, METAL PARTICLE DETECTING METHOD AND METAL PARTICLE DETECTING APPARATUS

[75] Inventors: Akira Mori; Ikuo Uchino; Atsuhiko Hirosawa; Kunihiro Yamazaki, all of Hiratsuka, Japan

[73] Assignee: Kabushiki Kaisha Komatsu Seisakusho, Tokyo, Japan

[21] Appl. No.: 232,235

[22] PCT Filed: Nov. 6, 1992

[86] PCT No.: PCT/JP92/01436

§ 371 Date: Jun. 23, 1994

§ 102(e) Date: Jun. 23, 1994

[87] PCT Pub. No.: WO93/09425

PCT Pub. Date: May 13, 1993

[30] Foreign Application Priority Data

Nov. 6, 1991 [JP] Japan ................................ 3-318412

[51] Int. Cl.$^6$ ................................................ G01N 27/06
[52] U.S. Cl. ................ 324/71.1; 324/446; 324/553; 324/722; 340/631; 361/301.4; 361/303
[58] Field of Search ..................... 324/446, 553, 324/686, 722, 754, 71.1, 71.4; 73/53.05, 53.07, 61.42, 61.71; 340/627, 631; 361/301.4, 303, 306.1, 308.1, 309, 328, 329, 330

[56] References Cited

U.S. PATENT DOCUMENTS

| 4,070,660 | 1/1978 | Tauber ................................ 340/236 |
| 4,127,808 | 11/1978 | Sproul et al. ........................ 324/65 R |

FOREIGN PATENT DOCUMENTS

| 54-43086 | 4/1979 | Japan. |
| 60-227159 | 11/1985 | Japan. |
| 3-282246 | 12/1991 | Japan. |
| 4-297864 | 10/1992 | Japan. |

Primary Examiner—Maura K. Regan
Assistant Examiner—Glenn W. Brown
Attorney, Agent, or Firm—Richards, Medlock & Andrews

[57] ABSTRACT

A metal particle detecting sensor (10), having a simple structure, can perform in-line analysis for metal particles in fluid and also can precisely estimate or detect the number of metal particles for each particle size. Metal films (1) and insulating films (2) are alternately laminated one upon another, and every other metal film (1) in the laminate is connected in parallel with one another to one of two lead wires (3a, 3b) so as to form comb electrodes in the laminate of the sensor, and one end face of the laminate is immersed in a fluid (4) containing metal particles so as to detect the metal particles.

20 Claims, 5 Drawing Sheets

METAL PARTICLE DETECTING SENSOR, METAL PARTICLE DETECTING METHOD AND METAL PARTICLE DETECTING APPARATUS

FIELD OF THE INVENTION

The present invention relates to the technology of detection of metal particles, which is suitable for detecting metal shavings or the like in lubrication oil, and in particular, to a metal particle detecting sensor, a method of detecting metal particles, and a metal particle detecting apparatus with which an in-line analysis can be made with a simple structure, and further, which can precisely determine the number of particles for every particle size.

TECHNICAL BACKGROUND

Heretofore, an analyzing laboratory or an in-line analyzer using typical metal particle detecting technology has employed one or more of the spectrophotometric, irradiation light attenuating, electrical resistance, and magnetic resistance types of metal particle detection technology. However, with this technology, the following problems have occurred:

(1) The spectrometric type technology can detect substantially all kinds of particles so as to obtain the quantity of particles in each of the kinds. However, a large scale detecting apparatus has to be used, and accordingly, it is not appropriate for use in in-line analysis. Furthermore, with this technology, it is impossible to estimate or detect the number of particles per particle size;

(2) The irradiation light attenuating type technology can detect substantially all kinds of particles so as to obtain the quantity of particles in each of the kinds, and it is suitable for use in in-line analysis. However, it is impossible to estimate or detect the number of particles per particle size.

(3) The electrical resistance type technology is suitable for use in in-line analysis, but its detection errors are large. Further, it is impossible to estimate or detect the number of particles per particle size.

(4) The magnetic resistance type technology is suitable for use in in-line analysis. However, it cannot detect particles other than ferromagnetic material particles such as Fe or Ni. Furthermore, it is impossible to estimate or detect the number of particles per particle size.

Further, in Japanese Patent Application No. 2-83150, the inventors have proposed a metal particle detecting sensor with a simple structure using electric discharge. However, since a pair of comb electrodes used in this metal particle detecting sensor are composed of a pair of platinum thin film electrodes formed on an insulator by a vapor deposition process or the like, being slightly spaced from each other, it cannot estimate or detect the number of metal particles, in fluid, per particle size.

SUMMARY OF THE INVENTION

One object of the present invention is to provide a metal particle detecting sensor, a metal particle detecting method, and a metal particle detecting apparatus, with which metal particles in fluid can be analyzed in-line with a simple structure, and which can precisely estimate or determine the number of metal particles per particle size.

According to a first aspect of the present invention, there is provided a metal particle detecting sensor in which metal films and insulating films are alternately laminated one upon another, and every other one of the metal films is connected in parallel, by a respective one of two lead wires, so as to form two comb electrodes in the laminate, whereby an end face of the laminate can be immersed in a fluid containing metal particles for detecting the metal particles.

According to a second aspect of the present invention, there is provided a method of detecting metal particles, in which the above-mentioned metal particle detecting sensor is used so as to detect pulse voltages V, then a number f(v) of pulses per identical voltage V among the thus detected pulse voltages V is computed, and then for every identical voltage, computation is carried out with the following expressions:

$$k_1 \times V^{1/2} = r$$

$$k_2 \times f(v) \times V^{1/2} = Pn$$

whereby the thus obtained estimated particle number Pn per estimated particle size is regarded as being analogous to or identical with an actual number N of particles per actual particle size R in a fluid to be detected, where $k_1$ and $k_2$ are predetermined constants.

According to a third aspect of the present invention, there is provided a metal particle detecting apparatus comprising the above-mentioned metal particle detecting sensor, a processing unit connected to the metal particle detecting sensor, and an output unit connected to the processing unit, the processing unit storing in memory a constant $k_1$ which has been previously set corresponding to at least the metal particle detecting sensor, and a constant $k_2$ which has been previously set corresponding to at least the metal particle detecting sensor and a detection time, the processing unit receiving pulse voltages V from the metal particle detecting sensor so as to count a number f(v) of pulses per identical voltage V, and then computing, per identical voltage V, the following expressions:

$$k_1 \times V^{1/2} = r$$

$$k_2 \times f(v) \times V^{1/2} = Pn$$

regarding that the thus obtained estimated number Pn of particles per estimated particle size r is resemblant to or identical with an actual number N of particles per actual particle size R for metal particles in a fluid to be detected, and accordingly delivering the thus obtained result to the output unit.

With this arrangement having a simple structure, it is possible to carry out an in-line analysis, and further, it is possible to precisely determine the number of metal particles per particle size.

BEST MODE FOR CARRYING OUT THE PRESENT INVENTION

The present invention has been devised and completed on the basis of several experiments and the results therefrom, and an explanation will be detailed hereinbelow.

Figure 7A:
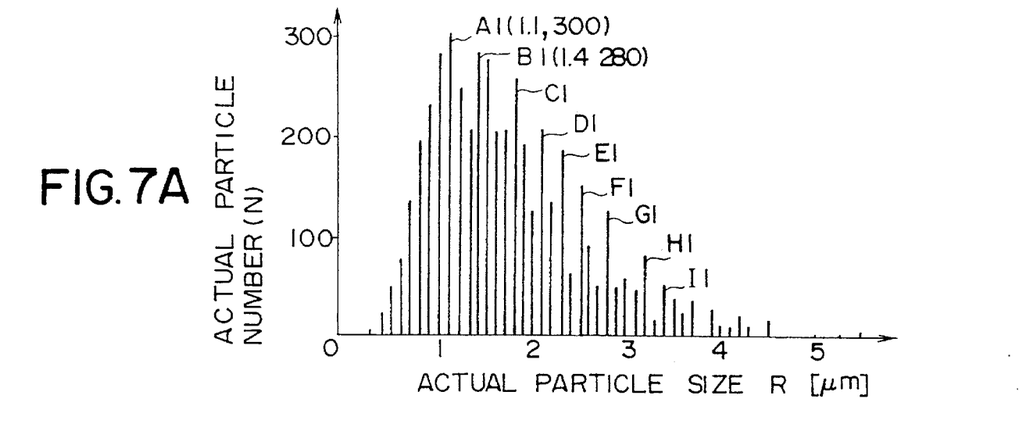
FIG. 7A is a chart showing the distribution of an actual number of particles per actual particle size.

Metal particles were manually sorted into several groups, each group having a number N of particles for every identical particle size R when they were observed through a microscope. FIG. 7A shows the result of this stratification, in which the actual particle size R is indicated on the axis of abscissa, and the actual number N of particles per particle size is indicated on the axis of ordinate.

Then, the metal particles were mingled into lubrication oil in a container, and were then suspended in the lubrication oil by the application of ultrasonic waves. While the suspension was held effectively, the container was set on a hot-plate for heating to a temperature of 80° C. in order to simulate an actual operation of an engine or the like.

Figure 7B:
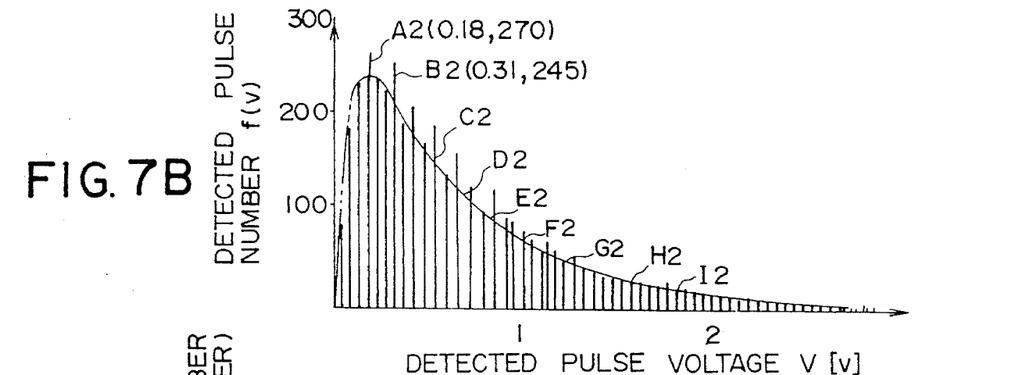
FIG. 7B is a chart showing the distribution of a number of detected pulses per detected pulse voltage obtained by the metal particle detecting sensor.

Next, a metal particle detecting sensor which will be hereinbelow detailed was immersed in the lubrication oil containing the metal particles so as to detect pulse voltages V. FIG. 7B shows a result of detection for fifty minutes, in which the detected pulse voltage V is indicated on the axis of abscissa, and the number f(v) of detected pulses per identical voltage V is indicated on the axis of ordinate.

By the way, the correlation between FIG. 7A and FIG. 7B is not readily apparent even though they are compared with each other. The inventors perceived that current runs in proportion to the square of a sectional area of a conductor, and derived the following expressions through their insight that should predetermined relational expressions be formulated, the voltages V of detected pulses shown in FIG. 7B could be converted into the actual particle size R shown in FIG. 7A, and then the number f(v) of detected pulses could be converted into the actual number N shown in FIG. 7A:

$$k_1 \times V^{1/2} = r \quad (1)$$

$$k_2 \times f(v) \times V^{1/2} = Pn \quad (2)$$

It is noted that the inventors considered that $V^{1/2}$ is indispensable in the expression (1) since current runs in proportion to the square of the sectional area of a conductor, and accordingly, it was introduced into the expression (1).

As to the expression (2), the inventors considered that the expression (2) is a function of the expression (1) in view of the analogy in external appearance between FIG. 7A and FIG. 7B, and introduced the value $V^{1/2}$ in the expression (2). Further, since the value f(v) is a number of pulses itself, the inventors, of course, introduced this value in the expression (2).

Figure 7C:
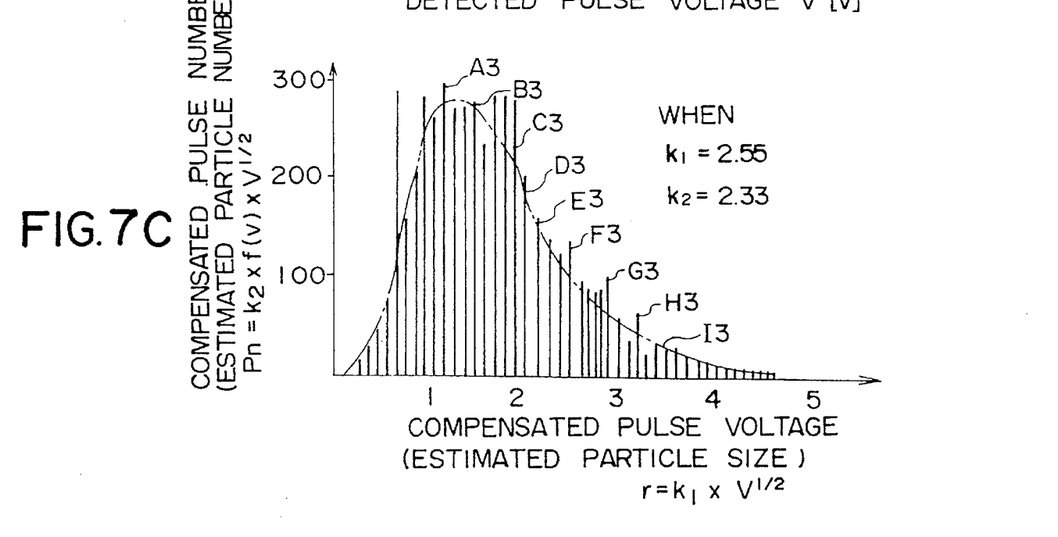
FIG. 7C is a chart of the distribution of an estimated number of particles per estimated particle size obtained by the metal particle detecting method and the metal particle detecting apparatus.

FIG. 7C is a chart obtained in accordance with the expressions (1) and (2). Values which are obtained by compensating the pulse voltages V shown in FIG. 7B with the use of the expression (1) correspond to the estimated particle sizes r indicated on the axis of abscissa in FIG. 7C, and values which are obtained by compensating the detected pulses numbers f(v) shown in FIG. 7B with the use of the expression (2) correspond to the estimated particle number Pn indicated on the axis of ordinate in FIG. 7C. A comparison between FIG. 7C and FIG. 7A reveals that they are resemblant to or identical with each other, and accordingly, it is possible to appreciate a correlation therebetween.

It is noted here that the wording "resemblant" means that even the number of particles per particle size can be precisely estimated, as stated in the object of the present invention, that is, the distribution of particle numbers for respective particle sizes can be determined. Further, the wording "identical" means that the particle number per particle size can be precisely detected, as stated in the object of the present invention, that is, the distribution of the particles can be detected so as to specify at least the units of the particle sizes and the particle number.

More specifically, if the constants are set as $k_1 = 2.55$ and $k_2 = 2.33$, FIG. 7A and FIG. 7C become identical with each other. That is, the estimated particle sizes r shown in FIG. 7C, which are obtained by compensating the detected pulse voltages V shown in FIG. 7B with the use of the expression (1), come to be coincident with the actual particle sizes R indicated on the axis of abscissa shown in FIG. 7A if the unit [V] is merely changed into [μm]. Meanwhile, the estimated particle numbers Pn which are obtained by compensating the detected pulse numbers f(v) shown in FIG. 7B with the use of the expression (2) come to be coincident with the actual particle numbers N indicated on the axis of the ordinate shown in FIG. 7A. That is, it can be said that FIG. 7C and FIG. 7A are "identical" with each other.

If the constants are set to other values, that is, $k_1 = 2.55$ and $k_2 = 0.233$, FIG. 7C is only resemblant to FIG. 7A, and accordingly, not only the actual particle sizes R but also the actual particle numbers N cannot be known, although the condition of the distribution of the particle numbers for respective particle sizes can be known. It can be said that such a case is "resemblant". Whether it is "resemblant" or "identical" in other words, "estimated" or "detected" is dependent upon the set values selected for the constants $k_1$, $k_2$.

Setting of the constants $k_1$ and $k_2$ is made in comparison of the actual particle sizes R and the actual particle numbers N shown in FIG. 7A with the detected pulse voltages V and the detected pulse numbers f(v) shown in FIG. 7B. That is, the point $A_1(1.1, 300)$ and the point $B_1(1.4, 280)$ in FIG. 7A correspond to the point $A_2(0.18, 270)$ and the point $B_2(0.31, 245)$ in FIG. 7B, respectively.

Accordingly, if r in the expression (1) is set as =R, a value of $k_1 \approx 2.59$ is obtained from the points $A_1$ and $A_2$, while a value of $k_1 \approx 2.51$ is obtained from the points $B_1$ and $B_2$; and by averaging them, $k_1 \approx 2.55$ is finally obtained. Further, if Pn is set as =N in the expression (2), a value of $k_2 \approx 2.62$ is obtained from the points $A_1$ and $A_2$, while a value of $k_2 \approx 2.05$ is obtained from the points $B_1$ and $B_2$; and by averaging them, a value of $k_2 \approx 2.33$ is finally obtained.

Thus, if the constants $k_1$ and $k_2$ are previously and precisely determined in accordance with a sample, the "identical" detection can be made. It is noted that the constants $k_1$ and $k_2$ are mainly determined in accordance with the thickness of insulating films 2, and the same constants $k_1$ and $k_2$ can be used for metal particle detecting sensors having the same specification. On the contrary, in the case of "estimation", the setting can be made as $k_1=k_2=1$.

The setting of the constants $k_1$ and $k_2$ can be suitably determined in dependence upon a required degree of accuracy for detection.

It is noted that the constant $k_1$ has to be set in consideration of at least the metal particle sensor to be used, and the constant $k_2$ has to be set in consideration of not only the metal particle detecting sensor to be used, but also a detection time. This detection time was set to fifty minutes in the experiments. However, should the detection time be set to one minute, $k_2=2.33\times 50=116.5$ should be set.

Figure 1:
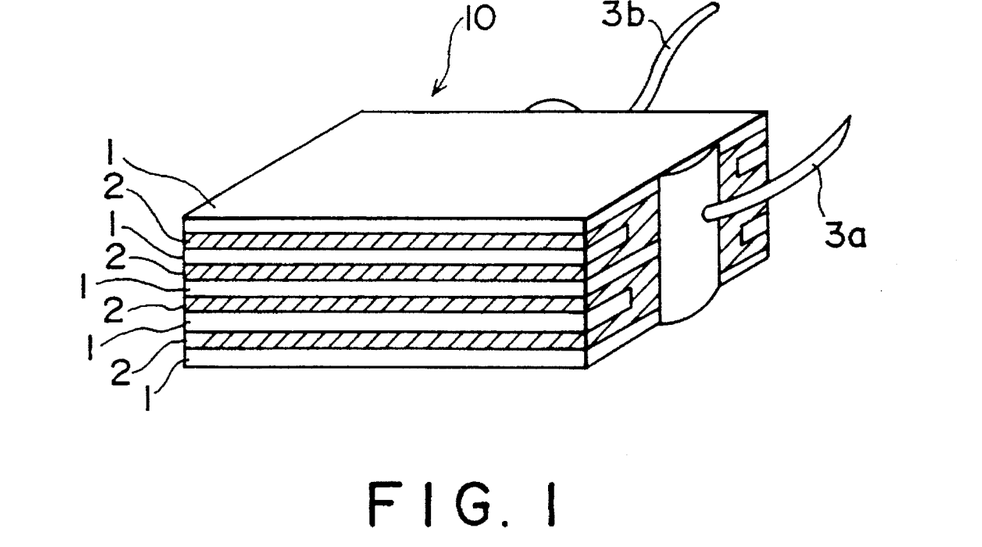
FIG. 1 is a schematic perspective view illustrating a metal particle detecting sensor according to one embodiment of the present invention.

Next, a detailed explanation will be made of a preferred embodiment of the present invention with reference to the drawings. Referring to FIG. 1 which is a schematic perspective view illustrating a metal particle detecting sensor 10 in one embodiment of the present invention, metal films 1 having a thickness of 10μm and insulating films 2 having a thickness of 10μm are alternately laminated one upon another. Every other metal film 2 is connected to a respective one of two lead wires 3a, 3b in parallel with one another so as to obtain comb electrodes in the cross-section of the lamination of the films. Further, an end face of the laminate is adapted to be immersed in a fluid containing metal particles.

Figure 2A:
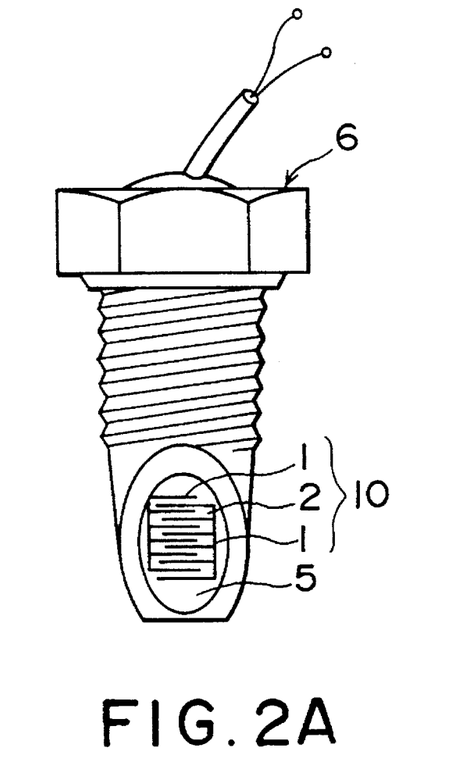
FIG. 2A is a front view illustrating an application of the metal particle detecting sensor shown in FIG. 1.
Figure 2B:
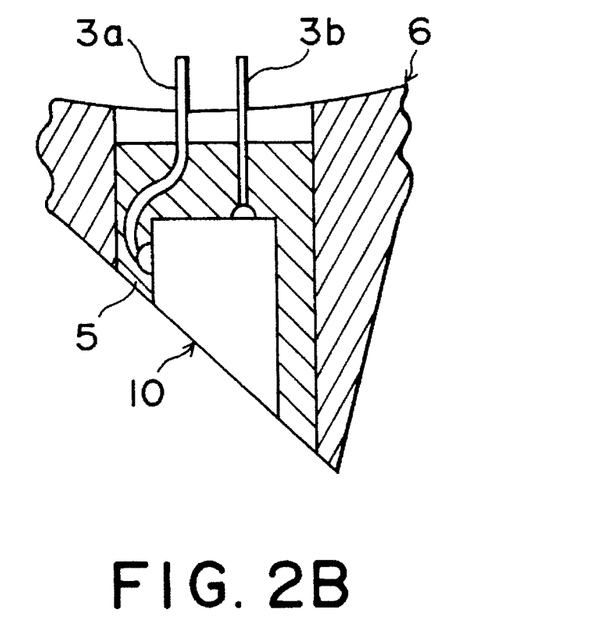
FIG. 2B is an enlarged sectional view illustrating a part of the metal particle detecting sensor shown in FIG. 1.
Figure 2C:
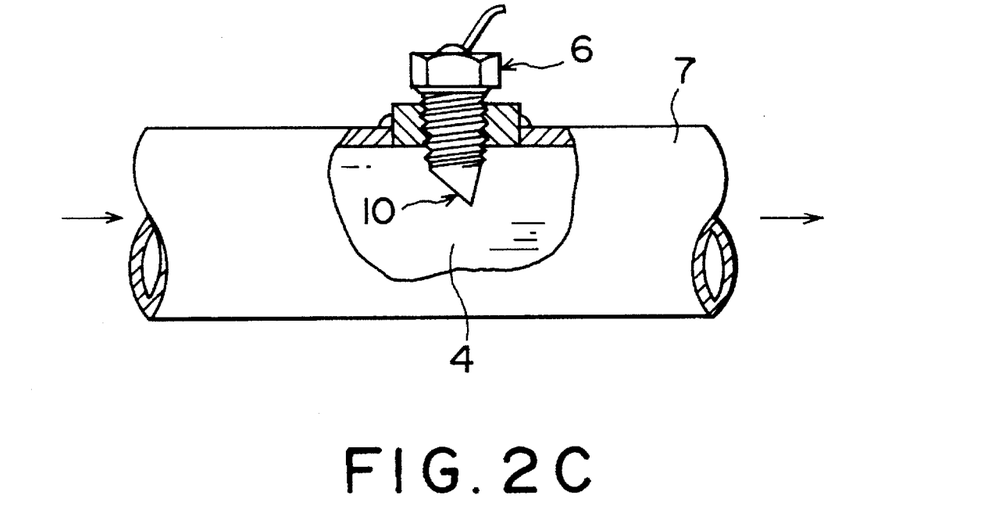
FIG. 2C is a view illustrating a condition in which the metal particle detecting sensor is installed.

Referring to FIGS. 2A and 2B, which are front and enlarged sectional views, respectively, illustrating an example of an application of the metal particle detecting sensor 10 and a part thereof, the metal particle detecting sensor 10 is incorporated in a screw plug type sensor body 6 and is surrounded by an insulator 5, excepting an end face of the laminate, and the lead wires 3a and 3b are led out from the sensor body 6. Referring to FIG. 2C, which is a view illustrating the mounting of the screw plug type sensor body 6, the screw plug type sensor body 6 is screwed into the outer wall of a tube 7 through which a fluid 4 flows. The metal particle detecting sensor 10 is positioned so that the end face of the laminate of the metal particle detecting sensor 10 is directed upstream with respect to the direction of flow of the fluid 4, and in this condition, an in-line analysis is carried out.

Figure 3A:
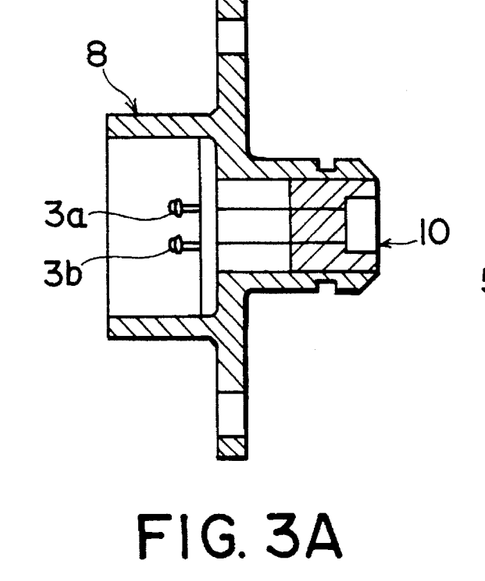
FIG. 3A is a sectional view illustrating another application of the metal particle detecting sensor.
Figure 3B:
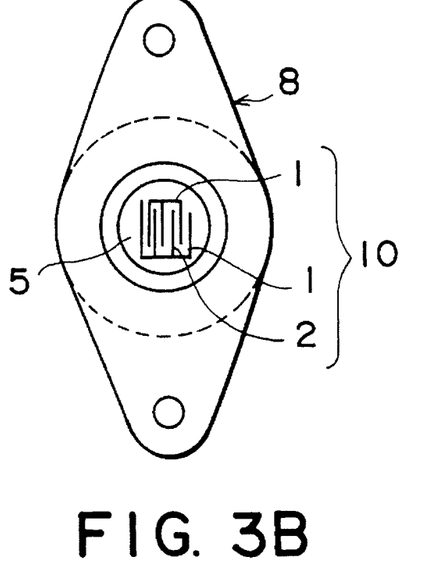
FIG. 3B is a front view illustrating the metal particle detecting sensor shown in FIG. 3A.
Figure 3C:
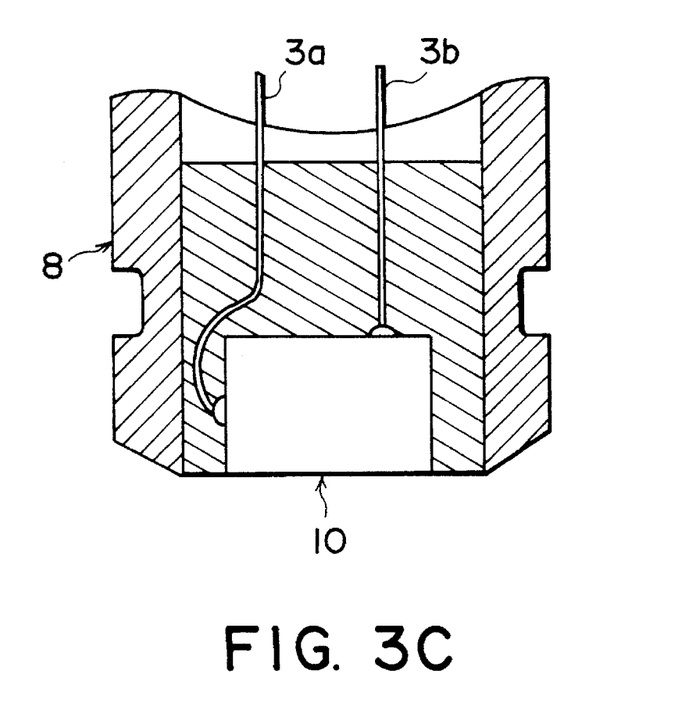
FIG. 3C is an enlarged sectional view illustrating a part of the metal particle detecting sensor shown in FIG. 3A.

FIGS. 3A and 3B are sectional and front views, respectively, illustrating another example of an application of the metal particle detecting sensor 10. The metal particle detecting sensor 10 is incorporated in a bolt type sensor body 8 and is surrounded by an insulator 5, excepting one end face of the laminate, and the lead wires 3A, 3B are led out therefrom. FIG. 3C is an enlarged view illustrating a part of FIG. 3A. In this case, the metal particle detecting sensor 10 is arranged so that the end face of the laminate of the metal particle detecting sensor 10 is directed upstream with respect to the direction of flow of a fluid 4, and in this condition, an in-line analysis is made.

Figure 4:
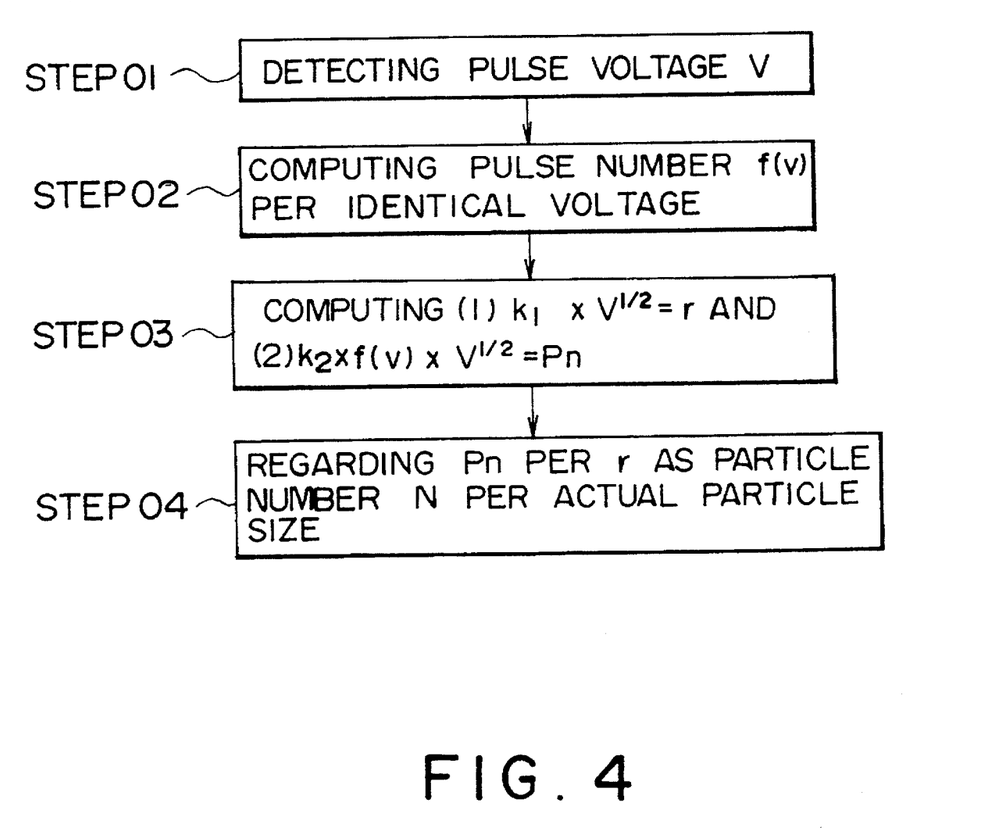
FIG. 4 is a flow chart for explaining a metal particle detecting method according to a second embodiment of the present invention.

Next, explanation will be made of a metal particle detecting method according to a second embodiment of the present invention with reference to FIG. 4 which is a flow chart. At first, pulse voltages V are detected by the metal particle detecting sensor 10 (step 01), then a pulse number $f(v)$ is counted for every identical voltage V (step 02), and thereafter, for every identical voltage V, the following expressions are computed (step 03):

$$k_1 \times V^{1/2} = r \quad (1)$$

$$k_2 \times f(v) = V^{1/2} = Pn \quad (2)$$

The thus obtained estimated particle number Pn per estimated particle size is regarded to be resemblant to or identical with the actual number N of particles in the fluid 4 to be detected per actual particle size R.

With such a metal particle detecting method, even the number of metal particles for each particle size can be precisely detected.

Figure 5:
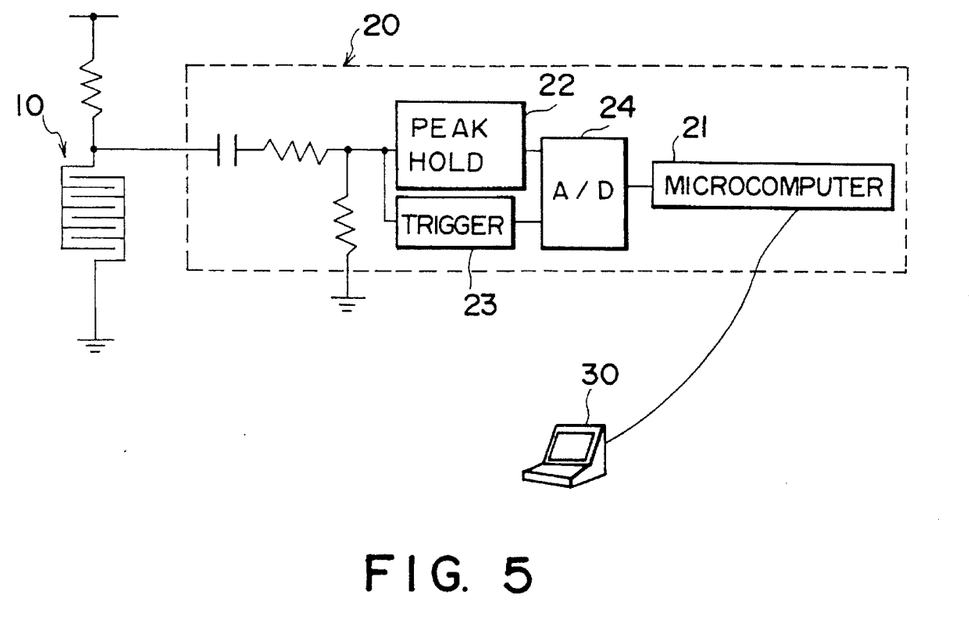
FIG. 5 is a block diagram illustrating a metal particle detecting apparatus according to a third embodiment of the present invention.
Figure 6:
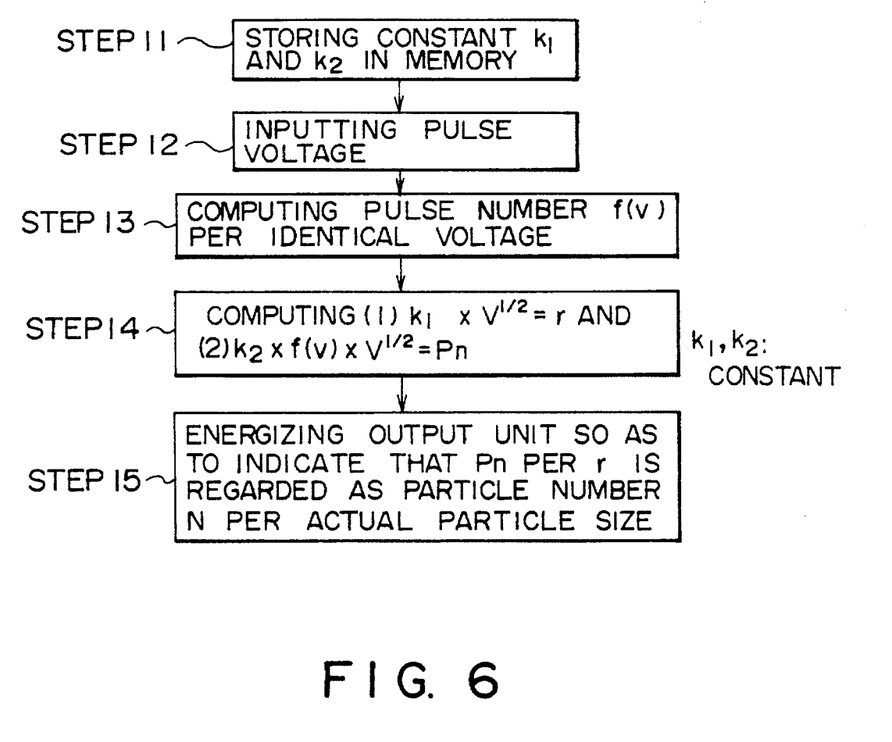
FIG. 6 is a flow chart for explaining the detection of metal particles with the use of the apparatus shown in FIG. 5.

Next, explanation will be made of a metal particle detecting apparatus according to a third embodiment of the present invention with reference to FIGS. 5 and 6. FIG. 5 is a block diagram illustrating the connection among a metal particle detecting sensor 10, a processing unit 20, and an output unit 30. In order to count detected pulses for every peak value for carrying out computation for graphic display on the output unit 30, the processing unit 20 receives signals from a peak-hold circuit 22 for holding a peak value of a detected pulse, and a trigger circuit 23 for specifying a detection time, and delivers them to a microcomputer 21 through an A/D converter 24. A voltage of 50 V is applied to the comb electrodes of the metal particle detecting sensor 10. By the way, since the maximum possible conversion voltage of the A/D converter 24 is 10 V, a pulse voltage delivered from the metal particle detecting sensor 10 is lowered down to ⅕ thereof. It is noted that the resistances can be used for limiting current.

With this arrangement, pulse waves can be observed from the metal particle detecting sensor 10. Accordingly, the processing unit 20 carries out a process corresponding to the flow chart shown in FIG. 6. At first, a constant $k_1$, previously determined in accordance with at least the metal particle detecting sensor 10, and a constant $k_2$, previously determined in accordance with at least the metal particle detecting sensor 10 and the detection time, are stored in memory (step 11). Then, pulse voltages V are inputted from the metal particle detecting sensor 10 (step 12), and thereafter, with these detected pulse voltages V, a pulse number $f(v)$ per detected pulse voltage is counted (step 13). Next, for every identical voltage, the following expressions are computed (step 14):

$$k_1 \times V^{1/2} = r \quad (1)$$

$$k_2 \times f(v) = V^{1/2} = Pn \quad (2)$$

Then, the thus obtained estimated article number Pn per estimated particle size r is regarded to be resemblant to or identical with the actual number of particles in the fluid 4 to be detected per actual particle size R, and the result is delivered from the output unit 30 (step 15). With this process, a result shown in FIG. 7C can be obtained, that is, it is possible to detect the number of metal particles per particle size with a high degree of accuracy.

Incidentally, it is possible to output either a mere numeric value or an image from the output unit 30. Further, in the case of the use of the metal particle detecting apparatus itself for an in-line analysis, a threshold value $r_0$ can be previously stored in the processing unit 20 if the particle number Pn is obtained for a predetermined estimated particle size, or a threshold value $Pn_0$ can be previously stored in the processing unit 20 if only the estimated particle number Pn is obtained. Further, computation is successively carried out for inputted pulse voltages V, and an alarm can be issued when $r=r_0$ and $Pn=Pn_0$ are obtained or when $Pn=Pn_0$ is obtained.

INDUSTRIAL APPLICABILITY

The present invention is to provide a metal particle detecting sensor having a simple structure which can perform in-line analysis for metal particles in fluid, and a metal particle detecting apparatus for estimating or detecting the number of particles for each particle size, and accordingly, is useful.

What is claimed is:

1. A metal particle detecting sensor comprising:

a plurality of metal films alternately laminated with a plurality of insulating films to form a laminate wherein adjacent metal films are separated from each other by an insulating film, said laminate having an end face;

a first lead connected to every other one of said metal films in said laminate to form a first comb electrode; and a second lead connected to the remaining metal films in said laminate to form a second comb electrode; and an insulator position so as to surround said laminate except for said end face of said laminate whereby in use said end face of said laminate can be immersed in a fluid containing metal particles in order for the sensor to detect the metal particles in the fluid and produce pulse voltages responsive to the thus detected metal particles.

2. A metal particle detecting sensor in accordance with claim 1, wherein each of said metal films has a thickness of about 10 µm.

3. A metal particle detecting sensor in accordance with claim 2, wherein each of said insulating films has a thickness of about 10 µm.

4. A metal particle detecting apparatus comprising:

a metal particle detecting sensor, a processing unit connected to said metal particle detecting sensor, and an output unit connected to said processing unit; wherein said metal particle detecting sensor comprises:

a plurality of metal films alternately laminated with a plurality of insulating films to form a laminate wherein adjacent metal films are separated from each other by an insulating film, said laminate having an end face;

a first lead connected to every other one of said metal films in said laminate to form a first comb electrode;

a second lead connected to the remaining metal films in said laminate to form a second comb electrode; and an insulator positioned so as to surround said laminate except for said end face of said laminate whereby in use said end face of said laminate is immersed in a fluid containing metal particles in order for the sensor to detect the metal particles in the fluid and produce pulse voltages responsive to the thus detected metal particles.

5. A metal particle detecting apparatus in accordance with claim 4, wherein said metal particle detecting sensor is mounted in a screw plug type sensor body.

6. A metal particle detecting apparatus in accordance with claim 5, wherein said screw plug type sensor body is mounted in a wall of a tube through which liquid flows, with said end face being exposed to the fluid and being directed upstream with respect to the direction of flow of the fluid in said tube.

7. A metal particle detecting apparatus in accordance with claim 6, wherein each of said metal films has a thickness of about 10 µm, and wherein each of said insulating films has a thickness of about 10 µm.

8. A metal particle detecting apparatus in accordance with claim 4, wherein said metal particle detecting sensor is mounted in a screw plug type sensor body.

9. A metal particle detecting apparatus in accordance with claim 8, wherein said bolt type sensor body exposes said end face to the fluid and with the end face being directed upstream with respect to the direction of flow of fluid.

10. A metal particle detecting apparatus in accordance with claim 9, wherein each of said metal films has a thickness of about 10 µm, and wherein each of said insulating films has a thickness of about 10 µm.

11. A metal particle detecting apparatus comprising a metal particle detecting sensor, a processing unit connected to said metal particle detecting sensor, and an output unit connected to said processing unit; wherein said metal particle detecting sensor comprises:

a plurality of metal films alternately laminated with a plurality of insulating films to form a laminate wherein adjacent metal films are separated from each other by an insulating film;

a first lead connected to every other one of said metal films in said laminate to form a first comb electrode; and a second lead connected to the remaining metal films in said laminate to form a second comb electrode;

whereby in use an end face of said laminate is immersed in a fluid containing metal particles to detect the metal particles;

wherein said metal particle detecting sensor detects the metal particles and establishes pulse voltages V with each pulse voltage V being representative of the size of a thus detected metal particle; wherein said processing unit counts, for each value of pulse voltage V, the number $f(v)$ of pulse voltages V among the thus detected pulse voltages V which are at least substantially identical to the respective value of pulse voltage V; wherein said processing unit computes, for each value of pulse voltage V, estimated particle sizes r for the respective value of pulse voltage V in accordance with the relationship $r=k_1 \times V^{1/2}$; and wherein said processing unit computes estimated particle numbers Pn in accordance with the relationship $Pn=k_2 \times f(v) \times V^{1/2}$; whereby the thus obtained estimated particle number Pn per estimated particle size is at least resemblant to the actual particle number N per actual particle size R.

12. A metal particle detecting apparatus in accordance with claim 11, wherein the value of each of $k_1$ and $k_2$ is such that said thus obtained estimated particle number Pn per estimated particle size is at least substantially identical to the actual particle number N per actual particle size R.

13. A method for determining the number of metal particles in a liquid and the particle size distribution of said metal particles, said method comprising the steps of:

using a metal particle detecting sensor in contact with a liquid containing metal particles to detect the metal particles and to establish pulse voltages V with each pulse voltage V being representative of the size of a thus detected metal particle;

for each value of pulse voltage V, counting the number $f(v)$ of pulse voltages V among the thus detected pulse voltages V which are at least substantially identical to the respective value of pulse voltage V;

for each value of pulse voltage V, computing estimated particle sizes r for the respective value of pulse voltage V in accordance with the relationship $r=k_1 \times V^{1/2}$;

computing estimated particle numbers Pn in accordance with the relationship $Pn=k_2 \times f(v) \times V^{1/2}$;

whereby the thus obtained estimated particle number Pn per estimated particle size is at least resemblant to the actual particle number N per actual particle size R.

14. A method in accordance with claim 13, wherein each of $k_1$ and $k_2$ is a constant, and further comprising the steps of determining the value of $k_1$ in accordance with at least the characteristics of said metal particle detecting sensor, and determining the value of $k_2$ in accordance with at least the characteristics of said metal particle detecting sensor and a detection time.

15. A method in accordance with claim 14, wherein the value of each of $k_1$ and $k_2$ is determined so that said thus obtained estimated particle number Pn per estimated particle size is at least substantially identical to the actual particle number N per actual particle size R.

16. A method in accordance with claim 15, further comprising storing in memory the value of each of $k_1$ and $k_2$.

17. A method in accordance with claim 16, wherein said metal particle detecting sensor comprises:

a plurality of metal films alternately laminated with a plurality of insulating films to form a laminate wherein adjacent metal films are separated from each other by an insulating film;

a first lead connected to every other one of said metal films in said laminate to form a first comb electrode; and a second lead connected to the remaining metal films in said laminate to form a second comb electrode;

whereby in use an end face of said laminate is immersed in a fluid containing metal particles to detect the metal particles.

18. A method in accordance with claim 13, wherein the value of each of $k_1$ and $k_2$ is determined so that said thus obtained estimated particle number Pn per estimated particle size is at least substantially identical to the actual particle number N per actual particle size R.

19. A method in accordance with claim 13, further comprising storing in memory the value of each of $k_1$ and $k_2$.

20. A method in accordance with claim 13, wherein said metal particle detecting sensor comprises:

a plurality of metal films alternately laminated with a plurality of insulating films to form a laminate wherein adjacent metal films are separated from each other by an insulating film;

a first lead connected to every other one of said metal films in said laminate to form a first comb electrode; and a second lead connected to the remaining metal films in said laminate to form a second comb electrode;

whereby in use an end face of said laminate is immersed in a fluid containing metal particles to detect the metal particles.

* * * * *

UNITED STATES PATENT AND TRADEMARK OFFICE
CERTIFICATE OF CORRECTION

PATENT NO. : 5,596,266
DATED : January 21, 1997
INVENTOR(S) : Mori et al

It is certified that error appears in the above-indentified patent and that said Letters Patent is hereby corrected as shown below:

Column 7, line 25, change "position" to --positioned--.

Column 8, line 7, change "screw plug" to --bolt--.

Signed and Sealed this

Twelfth Day of August, 1997

*Attest:*

BRUCE LEHMAN

*Attesting Officer*   *Commissioner of Patents and Trademarks*